United States Patent [19]
Koehler et al.

[11] Patent Number: 5,717,111
[45] Date of Patent: Feb. 10, 1998

[54] PROCESS FOR THE CONTINUOUS PREPARATION OF MACROCYCLIC COMPOUNDS

[75] Inventors: Guenther Koehler, Marl; Marcel Feld, Kolen; Josef Metz, Marl, all of Germany

[73] Assignee: Huels Aktiengesellschaft, Marl, Germany

[21] Appl. No.: 618,441

[22] Filed: Mar. 8, 1996

[30] Foreign Application Priority Data

Apr. 29, 1995 [DE] Germany .................. 195 15 888.1

[51] Int. Cl.⁶ .................................................. C07D 313/00
[52] U.S. Cl. .................................................. 549/266
[58] Field of Search .................................................. 549/266

[56] References Cited

U.S. PATENT DOCUMENTS

| | | | |
|---|---|---|---|
| 2,092,031 | 9/1937 | Spanagel | 260/123 |
| 4,105,672 | 8/1978 | Rueter et al. | 260/340.2 |
| 4,165,321 | 8/1979 | Harris et al. | 260/340.2 |
| 4,393,332 | 7/1983 | Harris | 549/266 |
| 4,709,058 | 11/1987 | Cahill, Jr. et al. | 549/267 |
| 4,803,288 | 2/1989 | Kitamura et al. | 549/267 |

FOREIGN PATENT DOCUMENTS 0 260 680    3/1988    European Pat. Off.

OTHER PUBLICATIONS

Database WPI Derwent Publications, AN–80–77899cm JP–A–55 120 581, Sep. 18, 1980.

*Primary Examiner*—Amelia Owens
*Attorney, Agent, or Firm*—Oblon, Spivak, McClelland, Maier & Neustadt, P. C.

[57] ABSTRACT

Process for the preparation of macrocyclic compounds by condensation of at least difunctional compounds and subsequent thermal depolymerization in the presence of catalysts, wherein thermal depolarization is carried out in solvent of the formula $$R^1 + O-CH_2-CH_2 \frac{1}{n} O - R^2 \qquad I$$

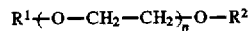

where $R^1$ and $R^2$ represent identical or different aliphatic $C_{1-6}$ hydrocarbon radicals with or without functional groups and having number average molecular weights (Mn) from 500 to 3,000, from which the value of n inevitably follows, at a pressure of less than 50 hPa and at a temperature of 200 to 300° C., 5 to 1,000 parts by weight of solvent being used per part by weight of macrocyclic compound.

13 Claims, No Drawings

PROCESS FOR THE CONTINUOUS PREPARATION OF MACROCYCLIC COMPOUNDS

BACKGROUND OF THE INVENTION

1. Field of the Invention

The present invention relates to a process for the preparation of macrocyclic compounds by condensation of at least difunctional compounds and subsequent thermal depolymerization in the presence of catalysts.

2. Discussion of the Background

Macrocyclic compounds, such as macrocyclic esters, play an extremely important role in the perfumery industry because of their known musk and ambergris notes and in addition as fixatives: The largest share of the market by volume is taken by the 15- to 18-membered lactones, dilactones or oxalactones.

Many processes are known for the preparation of these compounds, in which macrocyclic condensates can be prepared by thermolysis in vacuo at high temperatures in the presence of various metal catalysts. Thus, the depolymerization and cyclization products from the polycondensates are generally formed at very high temperatures (200° to 300° C.) and in vacuo. The macrocyclic compounds formed have a very high vapor pressure under these conditions, so that they can be removed from the system by distillation. The target products may be prepared in pure form and in perfumery quality by subsequent fractional distillation or by crystallization.

However, the choice of medium in which the reaction is carried out is often a problem. In EP-B 0 260 680 (U.S. Pat. No. 4,709,058), for example, olefin polymers, in JP-B 55-120 581 polyesters, polyether glycols, polyether glycol esters or only polyglycols, in DE-C 32 25 341 paraffin, are proposed as high-boiling media for depolymerization. However, all these substances have the disadvantage that they usually have a high melting point, which makes handling difficult. A serious disadvantage is that the polyether glycols and polyether glycol esters have functional groups which participate in the polymerization in an undesirable manner, which leads to considerable losses in yield.

A disadvantage of the paraffins is the usually too-low boiling point of these liquid-phase media, so that, during depolymerization at high temperatures and in vacuo, the liquid-phase medium can distill over together with the target product. As a result of this, an additional distillation stage often becomes necessary in the purification by distillation.

A requirement, important in the technique, is that the viscosity of the liquid-phase medium is low at temperatures beneath 50° C., so that, when the reaction is interrupted or terminated, the medium can readily be removed from the reactor, which is virtually impossible with known processes and conventional liquid-phase media.

Liquid-phase media such as paraffins or olefin polymers are, furthermore, solvents which are scarcely suitable for the linear polyesters or oligoesters. They frequently only disperse these, the particles being able to coagulate to form blocks. This is generally remedied by further dilution, which markedly reduces the space-time yield, as is the case in known processes.

In conventional and known processes, the cyclization is accompanied bypolycondensation as an undesirable side reaction (intermolecular cross-linking). This further increases the viscosity of the system, the stirrability and thermal conductivity of the mixture greatly decreasing. Adhesion to the walls and decomposition phenomena frequently occur, which have off-odor formation as a consequence. In the subsequent purification by distillation, these traces of odor impurities cannot be removed or can only be removed with very high losses.

The object of the present invention is to develop a preparation process for macrocyclic compounds which does not have these disadvantages.

SUMMARY OF THE INVENTION

The present invention relates to a process for the preparation of macrocyclic compounds comprising: a) condensation of at least difunctional compounds; and b) subsequent thermal depolymerization in the presence of catalysts, wherein thermal depolymerization is carried out in a solvent of the formula I

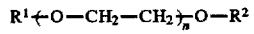

$$R^1 \text{-} (O\text{-}CH_2\text{-}CH_2)_n\text{-}O\text{-}R^2 \qquad I$$

where $R^1$ and $R^2$ represent identical or different aliphatic hydrocarbon radicals having 1 to 6 carbon atoms with or without functional groups and having number average molecular weights (Mn) from 500 to 3,000, from which the value of n inevitably follows, at a pressure of less than 50 hPa and at a temperature of 200° to 300° C., 5 to 1,000 parts by weight of solvent being used per part by weight of said condensed at least difunctional compound.

DETAILED DISCUSSION OF THE PREFERRED EMBODIMENTS

The high-boiling medium used for the thermal depolymerization is constituted by polyethylene glycol dialkyl ethers having number average molecular weights (Mn) of between 500 and 3,000, but preferably between 1,000 and 2,000, the terminal OH groups of the polyethylene glycol dialkyl ethers being etherified with $C_{1-6}$ alkyl groups.

The alkyl groups $R^1$ and $R^2$ etherifying the polyglycol can be, for example, methyl, ethyl, isopropyl, n-propyl, n-butyl or sec-butyl groups. The alkyl groups $R^1$ and $R^2$ may be further substituted with functional groups, wherein it is preferable that the functional groups do not participate in polymerization. Use can be made of mixtures of different polyethylene glycol dialkyl ethers and of polyethylene glycol dialkyl ethers etherified by different alkyl groups.

It was surprising that the solvents used according to the invention are stable in the presence of Lewis acids under the depolymerization reaction conditions. This could not be expected, since conventional ethers are known to split in the presence of Lewis acid at high temperatures.

It is effective, if at least 5 to 1,000 parts by weight of polyethylene glycol dialkyl ether, preferably from 10 to 100 part by weight, are used per 1 part by weight of the condensed at least difunctional compound.

In the depolymerization and cyclization of the linear oligomers, use is made of conventional catalysts and catalysts known from the prior art, such as alkali metals and salts thereof, magnesium salts, manganese salts, cadmium salts, iron salts, cobalt salts, tin salts, lead salts, aluminum salts and titanium salts. The amount of the catalyst, depending on the corresponding type used, is between 0.1 to 20% by weight, but preferably between 0.5 and 10% by weight, based on 100% by weight of condensed at least difunctional compound.

The process procedure is first initiated by the condensation of at least difunctional compounds, which can be performed according to conventional methods known to those of ordinary skill in the art at elevated temperatures with or without catalyst. The α,β-hydroxycarboxylic acid or α,β-dicarboxylic acid or ester of the same is reacted with a glycol. The alcohol or the water formed in this process is distilled off or removed using an entrainer or with the aid of a slight vacuum.

The present invention is suited for the depolymerization of linear polyesters accompanied by ring closure to form macrocyclic compounds. Polyesters employed for the process are obtained by conventional methods known to the art and are derived from conventional dicarboxylic acids, diols and hydroxymonocarboxylic acids. Dicarboxylic acids employed may be aliphatic and may be saturated or contain olefinic unsaturation and can be branched or straight-chain. Polyesters derived from aromatic or alicyclic dicarboxylic acids can also be employed, however.

The aliphatic dicarboxylic acids will typically contain from 3 up to about 18 carbon atoms and, more preferably, from about 8 to 14 carbon atoms. Useful dicarboxylic acids include, for example, malonic acid, maleic acid, succinic acid, glutaric acid, adipic acid, pimelic acid, azelaic acid, sebacic acid, undecanedioic acid, dodecanedioic acid, brassylic acid, pentadecanedioic acid, and the like. Mixtures of two or more dicarboxylic acids may also be employed.

Diols from which the polyesters are derived are primarily aliphatic diols having from 2 to 12, and more preferably, 2 to 6 carbon atoms. The diols may be saturated and can be either straight-chain or branched. Useful diols include ethylene glycol, 1,2- or 1,3-propanediol, 1,2-, 1,3-, or 1,4-butanediol, 1,6-hexanediol, 3-methyl-1,5-pentanediol, 2,3-dimethyl-2,3-butanediol, 1,8-octanediol, 2-ethylhexanediol, 1,10-decanediol, 1,12-dodecanediol, diethylene glycol, triethylene glycol, and the like. Alicyclic diols such as 1,4-cyclohexadimethanol may also be employed. Polyesters derived from ethylene glycol and di-, tri- and tetraethylene glycol are especially advantageous.

Hydroxymonocarboxylic acids from which useful polyesters can be derived include 15-hydroxypentadecanoic acid, 16-hydroxyhexadecanoic acid, 10-oxa-16-hydroxyhexadecanoic acid, 11-oxa-16-hydroxyhexadecanoic acid, 12-oxa-16-hydroxyhexadecanoic acid, 10-thia-16-hydroxyhexadecanoic acid, 11-thia-16-hydroxyhexadecanoic acid, 12-thia-16-hydroxyhexadecanoic acid, and the like.

Condensed at least difunctional compounds suitable for depolymerization and cyclization are described in U.S. Pat. No. 4,709,058, JP-B 55-120 581 and DE-C 32 25 341.

The condensed at least difunctional compound is then continuously transferred into the reactor, into which the high-boiling medium is introduced together with the catalyst component. The depolymerization and cyclization then take place at high temperatures of 200° to 300° C., preferably 220° to 265° C. and a vacuum of less than 50 hPa. The target product, under the above-mentioned conditions, distills over, the glycol (e.g. ethylene glycol) originating from the depolymerization or else a deliberate excess of glycol entraining the cyclic component.

After phase separation, the separated glycol can be fed back to the condensation at the beginning of the reaction. This material is also, moreover, advantageous since small amounts of dissolved macrocyclic compound are not lost from the material circulation in this manner.

Many macrocyclic compounds, such as esters, lactones, lactams, etherlactones, dilactones and etherdilactones, prepared by this process.

Illustrative macrocyclic products which can be conveniently produced by the depolymerization process of this invention include: 3,6,9-tridecamethylene malonate, dodecamethylene malonate, decamethylene malonate, ethylene suberate, ethylene azelate, 3-oxa-pentamethylene azelate, 3-methylpentamethylene sebacate, ethylene undecanedioate, ethylene dodecanedioate, ethylene brassylate, ethylene-alpha-methylbrassylate, ethylene-alpha,alpha-dimethylbrassylate, ethylene-alpha-ethylbrassylate, pentadecanolide, 12-oxa-pentadecanolide, 12-thia-pentadecanolide, hexadecanolide, 10-oxa-hexadecanolide, 11-oxa-hexadecanolide, 11-thia-hexadecanolide, 12-oxa-hexadecanolide and the like. The process of this invention is particularly advantageous for the preparation of ethylene brassylate and ethylene dodecanedioate by the depolymerization of polyethylene brassylate and polyethylene dodecanedioate, respectively.

The process is therefore particularly suitable for the preparation of macrocyclic esters and lactones having 6 to 20, preferably 8 to 15, carbon atoms since they can be produced in a particularly pure form by the process according to the invention, which greatly benefits their use as perfumes.

Having generally described this invention, a further understanding can be obtained by reference to certain specific examples which are provided herein for purposes of illustration only and are not intended to be limiting unless otherwise specified.

EXAMPLE 1

Preparation of a Linear Oligoester 460 parts of dodecanedioic acid and 1380 parts of ethylene glycol are heated under reflux for approximately 4 h at 160° to 200° C. with stirring and at atmospheric pressure. The water of reaction is then removed by distillation under a slight vacuum (approximately 500 hPa) or under a gentle nitrogen current. The linear oligoester (oligoethylene dodecanedioate) obtained in this manner has a freezing point of 25° to 35° C. and a very low degree of polymerization.

Preparation of a Cyclic Ester 200 g of this oligoethylene dodecanedioate (mean number average molecular weight Mn approximately 500) are metered in the course of 4 h into a flask having a distillation attachment and condenser which is charged with approximately 100 parts of polyethylene glycol dialkyl ether (mean number average molecular weight Mn 2,000) at a reduced pressure of 5 hPa and a temperature of 260° C.

Simultaneously, in the course of the same time, 0.5 g of the Sn-containing catalyst is metered as a solution in an inert solvent. Together with 147 g of ethylene glycol, 53 g of the cyclic ester of the dodecanedioic acid are then distilled over. This corresponds to a yield of approximately 93% of theory. After phase separation, the upper phase of the cyclic ester is subjected to precision distillation, the dilactone being obtained >99% in outstanding perfume quality virtually without losses. By recycling the lower ethylene glycol phase in which some of the cyclic ester is dissolved (approximately 5 to 7%), there are virtually no material losses.

The same liquid phase can be used in more than 50 of these cycles. After this, despite its relatively dark coloration, it is still fluid at 25° to 35° C. and can be removed from the reactor relatively easily. The reactor can easily be washed with solvents customary in the technique such as toluene or lower alcohols without adhesions to the walls being present.

EXAMPLE 2

Preparation of the Linear Oligoester 816 g (3 mol) of dimethyl tridecanedioate and 1,860 g (30 mol) of ethylene glycol are heated with stirring at atmospheric pressure and 160° C. in the liquid phase with or without a catalyst conventional for transesterification (e.g. p-toluenesulphonic acid). Under a slight vacuum (approximately 600 hPa) or a gentle nitrogen current, approximately 190 g of methanol are removed by distillation.

Preparation of the Cyclic Ester

In the course of 3 h, 185 g of the above-described oligoethylene tridecanedioate were metered, into an apparatus having a distillation attachment and cooler, into a 1 l flask which is charged with approximately 250 g of polyethylene glycol dimethyl ether (number average molecular weight Mn 2,000) and is at a reduced pressure of approximately 10 hPa and is heated to 260° C. At the same time, 0.3 g of a tin-containing catalyst are metered into the reactor. A mixture of 56 g of ethylene brassylate and 140 g of ethylene glycol then continuously distills over, which mixture separates into two phases. For complete extraction, ethylene brassylate can further be completely isolated from the lower ethylene glycol phase using a conventional extraction medium, a further 5 g being obtainable. The glycol phase can, at any rate, also be recycled to the process for preparing the oligoester without carrying out the extraction. By redistillation in high vacuum, the crude ethylene brassylate was brought to a purity of 99%, in which case 58 g were obtained at a yield of approximately 95% of the theory.

EXAMPLE 3

Preparation of the Oligomer Mixture

A mixture of 387 g (1.5 mol) of 15-hydroxypentadecanoic acid and 744 g (12 mol) of ethylene glycol were stirred together for 8 h at a liquid-phase temperature of 200° C., approximately 25 g of water distilling over together with small amounts of ethylene glycol. Removal of the water can be facilitated using a gentle nitrogen current. The oligomer mixture thus obtained is then used for the cyclization.

Cyclization Stage

The cyclization stage is carried out by metering 300 g of the above-described oligomer mixture together with 1 g of tetrabutyl titanate in the course of 6 h into a 1 l flask charged with approximately 300 g of polyethylene glycol dimethyl ether (number average molecular weight 1,500–2,000) and having a distillation attachment and cooler, at 250° C. and 5 hPa. At the same time, in the course of 6 h, a mixture of 295 g of cyclopentadecanolide and ethylene glycol distill over.

The mixture can be extracted using cyclohexane. An upper cyclohexane/cyclopentadecanolide phase and a lower ethylene glycol phase can be separated out. After removing the cyclohexane from the upper phase and distilling off the residue in vacuum, 91 g of cyclopentadecanolide are obtained having a purity of 99%, which corresponds to a yield of 93%.

Obviously, numerous modifications and variations of the present invention are possible in light of the above teachings. It is therefore to be understood that within the scope of the appended claims, the invention may be practiced otherwise than as specifically described herein. This application is based on German patent application DE 195 15 888.1, filed with the German Patent Office on Apr. 29, 1995, the entire contents of which are hereby incorporated by reference.

What is claimed as new and desired to be secured by Letters Patent of the United States is:

1. A process for the preparation of macrocyclic compounds comprising: a) condensation of at least difunctional compounds; and b) subsequent thermal depolymerization in the presence of catalysts, wherein said thermal depolymerization is carried out in a solvent of the formula

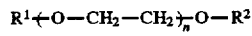

$$R^1 \!-\! (O\!-\!CH_2\!-\!CH_2)_n\!-\!O\!-\!R^2 \qquad I$$

where $R^1$ and $R^2$ represent identical or different aliphatic hydrocarbon radicals having 1 to 6 carbon atom with or without functional groups and said solvent having a number average molecular weight (Mn) of from 500 to 3,000, at a pressure of less than 50 hPa and at a temperature of 200° to 300° C., 5 to 1,000 parts by weight of said solvent being used per part by weight of condensed at least difunctional compound.

2. The process of claim 1, wherein said thermal depolymerization is carried out at a temperature of from 220° to 265° C.

3. The process of claim 1, wherein said macrocyclic compound is selected from the group consisting of lactones, and etherlactones.

4. The process of claim 1, wherein said macrocyclic compound is an ester or lactone having 6 to 20 carbon atoms.

5. The process of claim 1, wherein said macrocyclic compound is an ester or lactone having 8 to 15 carbon atoms.

6. The process of claim 1, wherein said catalyst is selected from the group consisting of alkali metals, salts of alkali metals, magnesium salts, manganese salts, cadmium salts, iron salts, cobalt salts, tin salts, lead salts, aluminum salts, titanium salts, and a mixture thereof.

7. The process of claim 1, wherein 0.1 to 20% by weight, based on 100% by weight of said condensed at least difunctional compound, of said catalyst is used.

8. The process of claim 1, wherein condensation of at least difunctional compounds occurs between dicarboxylic acids and diols.

9. The process of claim 1, wherein condensation of at least difunctional compounds is of a hydroxymonocarboxylic acid.

10. The process of claim 1, wherein condensation of at least difunctional compounds produces a linear polyester.

11. The process of claim 8, wherein said dicarboxylic acid is selected from the group consisting of malonic acid, maleic acid, succinic acid, glutaric acid, adipic acid, pimelic acid, azelaic acid, sebacic acid, undecanedioic acid, dodecanedioic acid, brassylic acid, pentadecanedioic acid and a mixture thereof.

12. The process of claim 8, wherein said diol is selected from the group consisting of ethylene glycol, 1,2-propanediol, 1,3-propanediol, 1,2-butanediol, 1,3-butanediol, 1,4-butanediol, 1,6-hexanediol, 3-methyl-1,5-pentanediol, 2,3-dimethyl-2,3-butanediol, 1,8-octanediol, 2-ethylhexanediol, 1,10-decanediol, 1,12-dodecanediol, diethylene glycol, triethylene glycol, 1,4-cyclohexadimethanol and a mixture thereof.

13. The process of claim 9, wherein said hydroxymonocarboxylic acid is selected from the group consisting of 15-hydroxypentadecanoic acid, 16-hydroxyhexadecanoic acid, 10-oxa-16-hydroxyhexadecanoic acid, 11-oxa-16-hydroxyhexadecanoic acid, 12-oxa-16-hydroxyhexadecanoic acid, 10-thia-16-hydroxyhexadecanoic acid, 11-thia-16-hydroxyhexadecanoic acid, 12-thia-16-hydroxyhexadecanoic acid and a mixture thereof.

* * * * *